United States Patent [19]

Maciejewski

[11] Patent Number: 5,596,133
[45] Date of Patent: Jan. 21, 1997

[54] ROTATING PEEL FIXTURE

[75] Inventor: Wendell C. Maciejewski, Salem, Conn.

[73] Assignee: The United States of America as represented by the Secretary of the Navy, Washington, D.C.

[21] Appl. No.: 521,387

[22] Filed: Aug. 23, 1995

[51] Int. Cl.⁶ ................................................. G01N 19/00
[52] U.S. Cl. .................... 73/7; 73/866; 73/150 A
[58] Field of Search ................ 73/7, 150 R, 150 A, 73/866, 431, 432.1; 211/163, 164, 166, 55, 56, 58, 70, 77, 78, 95, 115, 129, 131, 144

[56] References Cited

U.S. PATENT DOCUMENTS

| | | | |
|---|---|---|---|
| 3,985,026 | 10/1976 | Griffin et al. ............................. | 73/7 |
| 4,035,938 | 7/1977 | Neilsen ................................ | 211/58 X |
| 4,505,159 | 3/1985 | Entwistle ............................ | 73/866 X |
| 5,061,124 | 10/1991 | Chen ..................................... | 408/135 |
| 5,160,053 | 11/1992 | Graham et al. ........................ | 211/164 |

FOREIGN PATENT DOCUMENTS

| | | | |
|---|---|---|---|
| 0218051 | 10/1985 | Japan ........................................ | 73/150 |
| 0155241 | 6/1989 | Japan ........................................ | 73/150 |

*Primary Examiner*—Richard Chilcot
*Assistant Examiner*—Paul D. Amrozowicz
*Attorney, Agent, or Firm*—Michael J. McGowan; Michael F. Oglo; Prithvi C. Lall

[57] ABSTRACT

A U-shaped bracket has bearings holding a rotatable shaft. The shaft supports a pair of conical disks with their apexes facing each other along the shaft. Nuts are positioned along the shaft outside of the cones to position the cones. A cylindrical strength piece and a cylindrical test piece are inserted over the shaft with the test piece being outermost. The nuts tighten the disks against the test piece with the strength piece being of such a size to inhibit the disks from damaging the test piece. The bracket has an extension affixed to it that is attached to a testing machine. The cylindrical test piece is suitable for rotation and has a coating bonded to it. The testing machine peels the coating at a constant 90° angle from the test piece and measures the peel strength upon the test piece being rotated.

2 Claims, 2 Drawing Sheets

ROTATING PEEL FIXTURE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

The present invention generally relates to a fixture used for testing the bond strength of a coating affixed to the surface of a body. More particularly the fixture holds the body, that is cylindrical in shape, in an optimal position, throughout a process of peeling the affixed coating off. When used in conjunction with proper state-of-the-art instrumentation the inventive fixture provides a means for evaluating the peel strength of the adhesive bond between the coating and the cylindrical body. The inventive device is particularly suitable for use in measuring the peel strength of elastomeric coatings bonded to the outside of steel cylinders; the initial application being transducer bodies.

(2) Description of the Prior Art

The present invention relates to the measurement of the bonding of elastomers to the outside of different transducer bodies. All of the bodies are steel cylinders. It was found not to be conducive to test other geometric shapes as the condition of the materials, and the techniques used to apply the elastomer and adhesive, and the curing cycles all would be different. The resulting information would be different and not as valuable.

Other types of peel tests include flat plate tests. The angle of peel (90°) for a steel cylinder is essentially the same as that of a flat plate test. However, the details learned in applying the adhesive and rubbers to a steel cylinder which is the actual shape of the components to be used yields superior practical data.

There are two prior art variations of the flat plate 90° peel test. One uses a sliding plate fixture that holds a flat plate secure in a set of clamps. The fixture and sample are perpendicular to the angle of pull. The fact that the plate slides, maintains a constant angle relative to the pulling direction. The other test uses a flat plate that has one end bent into the shape of an L. Onto the surface of this plate is bonded the test material. The bent leg of the plate is gripped in a clamping fixture and held stationary. A flap of the elastomer is clasped in another grip and pulled away from the plate. A major disadvantage here is that the angle of pull is not constant and thereby provides semi-false information.

Also, in conjunction with peel tests for cylindrical bodies, dimensional accuracy is very critical. If the fixturing is inaccurate, the values will be in error. If the sample is skewed or twisted, the angle of pull will not be perpendicular to the test sample, and the bond-line will be twisted as well. Instead of the force acting on the bond-line straight across the width of the test sample (the shortest distance), it will act across a longer bond-line. This longer line of action will take a larger, erroneous force. It is also possible for the resulting mode of adhesive failure to be different.

SUMMARY OF THE INVENTION

Accordingly, it is a general purpose and object of the present invention to provide an improved test device for use in measuring the peel strength of coatings affixed to surfaces. It is a further object that the test device be of special applicability in testing peel strength of outer surfaces of cylindrically shaped acoustic transducers for torpedoes in present or anticipated use by the U.S. Navy. It is a further object that the test device be suitable for use with conventional instrumentation. It is a further object that the test device centers the test cylinders between conical disks and that the test cylinders and disks rotate freely with substantially no friction. A still further object is that the test device holds a cylindrical shell type sample piece free from buckling or collapsing on itself due to tightening of threaded fasteners used in mounting the sample piece to the test device. It is yet another object that the test device maintain a cylindrical shell type sample free to rotate, but with sufficient dimensional accuracy to assure a force acting on the coating will act on a bond line straight across the axial width of the coating. Yet, still another object is that the test device be provided with visual indicia enabling an operator to align a cylindrical shell type sample piece in concentric relation to the axis of rotation thereof with a high degree of accuracy. Other objects are that the test device is suitable to accommodate several sample sizes and is uncomplicated in structure for ease in building additional test devices for a large range of sizes in the test samples.

These objects are accomplished with the present invention by providing a structure having a pair of disks having conical surfaces suitable for holding a cylindrical test sample. The tips of the conical surfaces are on the cones axis. A shaft runs through the center of the cones and the test sample. A sturdy cylindrical piece fits radially outward of the shaft and inward of the test piece between the conical disks. The shaft also supports nuts for positioning and tightening the disks on the test piece. When this occurs the test piece is held fast and the sturdy cylindrical piece, radially inward of the test piece, is of such a size to prevent damage to the test piece. The shaft is mounted on a U-shaped bracket that is affixed to a piece that attaches to a test machine that is used to peel an affixed surface from the test piece and measure the peel strength of the bond.

BRIEF DESCRIPTION OF THE DRAWINGS

For a more complete understanding of the present invention and the advantages thereof, reference is now made to the following description of the preferred embodiment taken in conjunction with the accompanying drawings in which.

DESCRIPTION OF THE PREFERRED EMBODIMENT

Figure 1:
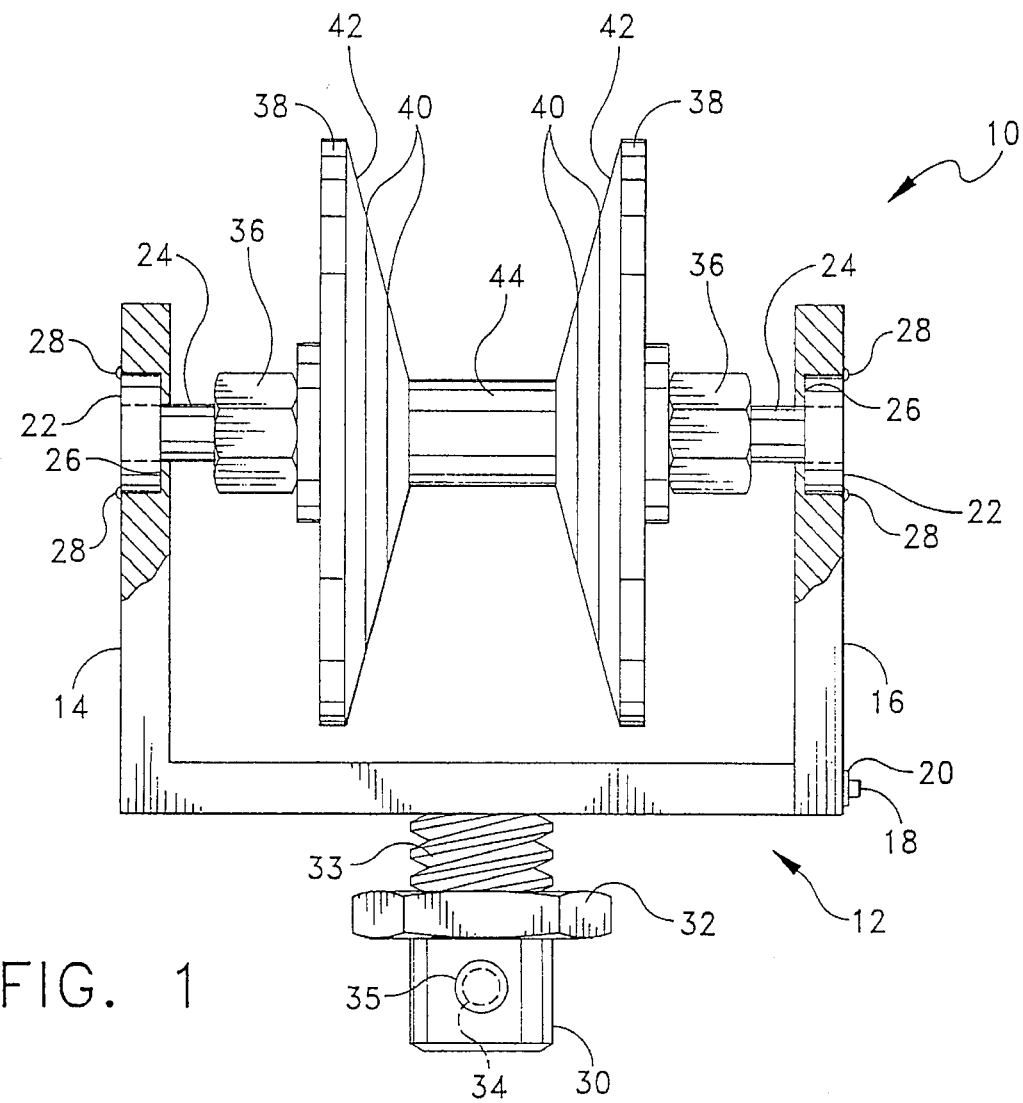
FIG. 1 is a front view of a rotating peel fixture in accordance with the present invention.

Refer now to the figures for a description of the components of the inventive rotating peel fixture 10. The fixture 10 has a base that is an aluminum U-shaped bracket 12 formed by an L-leg 14 and a rectangular leg 16. The rectangular leg 16 is affixed to the L-leg 14 by two screws 18 with washers 20. This makes the components readily detachable.

Figure 2:
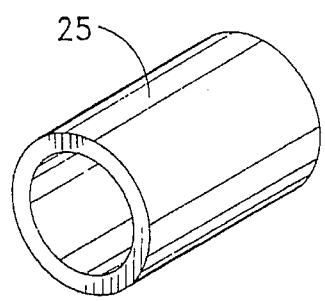
FIG. 2 is a view of a cylindrical test sample used on the rotating peel fixture of FIG. 1.
Figure 3:
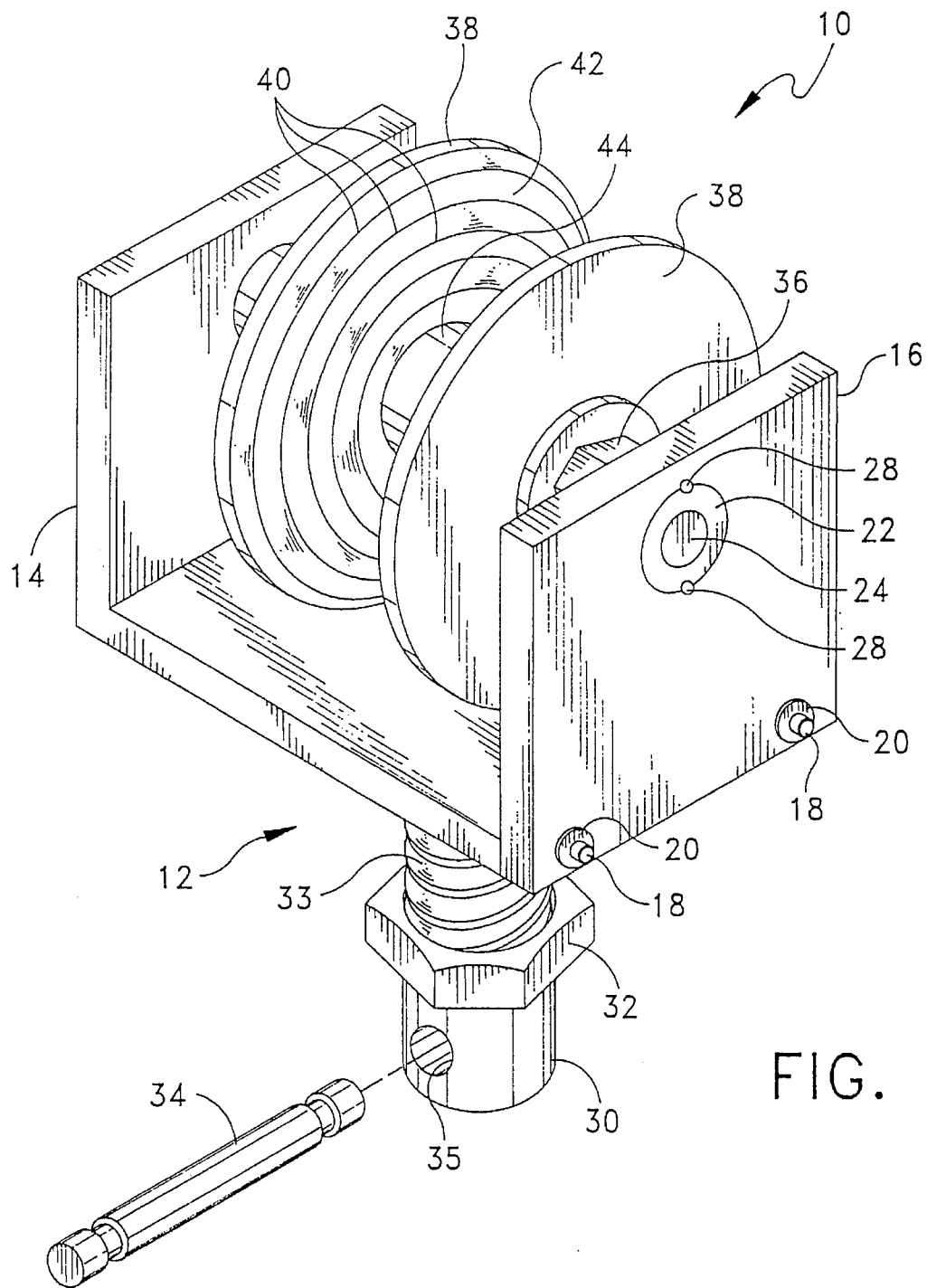
FIG. 3 is a perspective view of the rotating peel fixture of FIG. 1.

Each of the legs 14 and 16 has a bearing 22 assembled in it to accept a center shaft 24. The bearings 22 are located so that the center shaft 24 is held parallel to the base of the testing machine (not shown) and perpendicular to the angle of pull. The bearings 22 are held in place on a shoulder 26 in each leg 14, 16 by two screws 28. The bearings are located so that the center shaft 24 is held perpendicular to parallel sections of each leg 14, 16 and allows for substantially frictionless rotation of the center shaft 24 and subsequently of the test sample 25 shown in FIG. 2.

Attached to the L-leg 14 so that it is centered in the middle of the bottom of the U-shaped bracket 12 is an adapter shaft 30 with a lock nut 32 turning on threads 33. The adapter shaft 30 is particular to the type of loading machine used in conjunction with the rotating peel fixture 10. The adapter shaft 30 shown fits a standard Instron grip adapter. The crosshole 35 in the adapter shaft 30 is used to accept a pin 34 which rigidly secures the rotating peel fixture 10 to the Instron grip adapter. The lock nut 32 applies a slight preload to the Instron grip adapter. This provides stability and removes any play between the rotating peel fixture 10 and the Instron grip adapter.

The center shaft 24, in this particular fixture 10, was manufactured from a ¾ inch diameter steel bar. Both ends of the center shaft 24 are machined to be able to slip fit into the inside diameter of the bearings 22. The center shaft 24 is threaded to accept two shoulder nuts 36. The thread is chosen to allow for rapid hand tightening and ease in operation. In this case, the center shaft 24 was threaded at both ends for a distance of approximately 1⅜ inches with a ¾-10 UNC thread. There is an unthreaded portion measuring 1⅛ inches in the center of the shaft 24.

There are two centering conically shaped disks 38 used to support the test sample 25. The disks 38 are manufactured from aluminum and are substantially six inches in diameter. The disks 38 are tapered to a final thickness of ½ inch with an aperture in the center of each disk 38. Stated another way, disks 38 are each conically shaped. The aperture is for providing a loose fit with the center shaft 24. Both disks 38 have shallow concentric grooves 40 spaced about ⅛ inch apart along its tapered surface 42 for alignment purposes.

The test sample 25 is installed on the shaft 24 between the disks 38, radially outward of the spacer 44. The spacer 44 fits on the center shaft 24 between the two disks 38. This provides a fixed spacing for the test sample 25. The size of the spacer 44 is particular to the size of the test sample. The spacer 44 is sturdy and provides a fixed spacing so that the sample 25 can be pinched and tightly held between the disks 38. In addition, the spacer 44, functioning as a stop, is of such size and strength so that further tightening of the disks 38, by the nuts 36, on the test sample 25, that would ordinarily damage the test sample 25, cannot occur.

The shoulder nuts 36 position the disks 38, and the spacer 44 and test sample 25 to the middle of the center shaft 24. The shoulder nuts 36 are then tightened to lock the sample 25 in place.

There has therefore been described a fixture 10 that holds a cylindrical test sample 25 in a position that allows a bonded coating material to be peeled off of the cylindrical test sample 25 and the peel strength measured upon rotating the cylinder 25.

The conical mounting disks 38 prevent misalignment of the test sample 25 during mounting and during the actual testing. They eliminate the possibility of slipping during load application by wedge action. The concentric grooves 40 assist in aligning the sample 25 on both ends to eliminate the possibility of skewing the bond-line in turn causing erroneous results. The spacer 44 prevents the sample 25 from buckling or collapsing on itself due to tightening the shoulder nuts 36. Since the rotating shaft 24 is on bearings 22, friction is virtually eliminated from the system. It will be appreciated that friction can play an important part in the accurate reporting of loads. Any friction will increase the load, and this is undesired. The bearings 22 ensure that the loads reported are those of the bonds under test.

An alternative structural arrangement for removing the center shaft 24 from the fixture 10 to change test samples, to be tested, would be to split each of the legs 14, 16 across their width at a location halfway up on each of the bearings 22. This would allow the lifting out of the center shaft 24. It would also allow the lower part of the U-shaped bracket 12 to be built as one piece.

It will be understood that various changes in the details, materials, steps and arrangement of parts, which have been herein described and illustrated in order to explain the nature of the invention, may be made by those skilled in the art within the principle and scope of the invention as expressed in the appended claims.

What is claimed is:

1. A rotating peel fixture comprising:

a U-shaped bracket comprising an L-leg, a rectangular leg affixed to said L-leg, and a pair of bearings, with each of said legs holding one of said pair of bearings;

a shaft held by said pair of bearings in such a manner so that said shaft can be rotated with respect to said U-shaped bracket;

a pair of conically shaped disks slidably mounted on said shaft and having their conical surfaces facing each other;

adjusting means for positioning said pair of conically shaped disks on said shaft, said adjusting means further comprises a pair of shoulder nuts located on said shaft adjacent and outward of said conically shaped disks for positioning said conically shaped disks;

a cylinder having a predetermined axial length mounted on said shaft between said conical surfaces and having sufficient strength to place a stop on said conically shaped disks, thereby preventing said adjusting means from positioning said conical surfaces from each other at less than a distance determined by the axial length of said cylinder; an adapter shaft affixed to said L-leg at the middle bottom of said U-shaped bracket; and a lock-nut placed on said adapter shaft.

2. A rotating peel fixture comprising:

a U-shaped bracket;

a shaft held by said U-shaped bracket in such a manner so that said shaft can be rotated with respect to said U-shaped bracket;

a pair of conically shaped disks slidably mounted on said shaft and having their conical surfaces facing each other, a series of varied diameter circular indicia are scribed on the conical confronting surface of each of said pair of disks;

adjusting means for positioning said pair of conically shaped disks on said shaft; and a cylinder having a predetermined axial length mounted on said shaft between said conical surfaces and having sufficient strength to place a stop on said conically shaped disks, thereby preventing said adjusting means from positioning said conical surfaces from each other at less than a distance determined by the axial length of said cylinder.

* * * * *